(12) United States Patent
Kiehne

(10) Patent No.: US 7,104,400 B2
(45) Date of Patent: Sep. 12, 2006

(54) MEDICAL SYRINGE CONTAINER

(75) Inventor: Bruce Leigh Kiehne, Springwood (AU)

(73) Assignee: Occupational & Medical Innovations LTD., Slacks Creek (AU)

( * ) Notice: Subject to any disclaimer, the term of this patent is extended or adjusted under 35 U.S.C. 154(b) by 0 days.

(21) Appl. No.: 10/478,299

(22) PCT Filed: Mar. 25, 2003

(86) PCT No.: PCT/AU03/00361

§ 371 (c)(1),
(2), (4) Date: Dec. 2, 2003

(87) PCT Pub. No.: WO03/080467

PCT Pub. Date: Oct. 2, 2003

(65) Prior Publication Data

US 2004/0144669 A1 Jul. 29, 2004

(30) Foreign Application Priority Data

Mar. 25, 2002 (AU) ................................. PS1357

(51) Int. Cl.
*B65D 83/10* (2006.01)
(52) U.S. Cl. .................... 206/366; 206/571; 229/122.1
(58) Field of Classification Search ................ 116/212; 206/366, 370, 438, 570–572; 229/121, 122, 229/122.1; 248/153
See application file for complete search history.

(56) References Cited

U.S. PATENT DOCUMENTS

| 3,221,928 | A |   | 12/1965 | Horn |
|---|---|---|---|---|
| 3,804,293 | A | * | 4/1974 | Redman ..................... 221/102 |
| 3,809,287 | A | * | 5/1974 | Muller-Scherak ............ 221/66 |
| 3,880,321 | A | * | 4/1975 | Braginetz ..................... 221/66 |
| 4,415,092 | A | * | 11/1983 | Boyer ........................ 211/69.1 |
| 4,559,201 | A | * | 12/1985 | Yamada et al. ............... 422/63 |
| 5,152,394 | A |   | 10/1992 | Hughes |
| 5,190,185 | A |   | 3/1993 | Blechl |
| 5,277,312 | A |   | 1/1994 | Vumbaca |
| 5,291,997 | A |   | 3/1994 | He et al. |
| 5,740,909 | A |   | 4/1998 | Nazare et al. |
| 2003/0132129 | A1 |   | 7/2003 | Erickson |

FOREIGN PATENT DOCUMENTS

WO    PCT/US03/00778    1/2003

* cited by examiner

Primary Examiner—Jila M Mohandesi
(74) Attorney, Agent, or Firm—Hoffman, Wasson & Gitler, P.C.

(57) ABSTRACT

A medical syringe container comprising a housing, an outlet through which a new syringe can be removed from the housing, an inlet through which a syringe can be replaced into the housing, and holding means to prevent a second syringe from being removed from the housing until a used syringe has been replaced into the housing. The container is particularly useful with needle exchange programs.

9 Claims, 9 Drawing Sheets

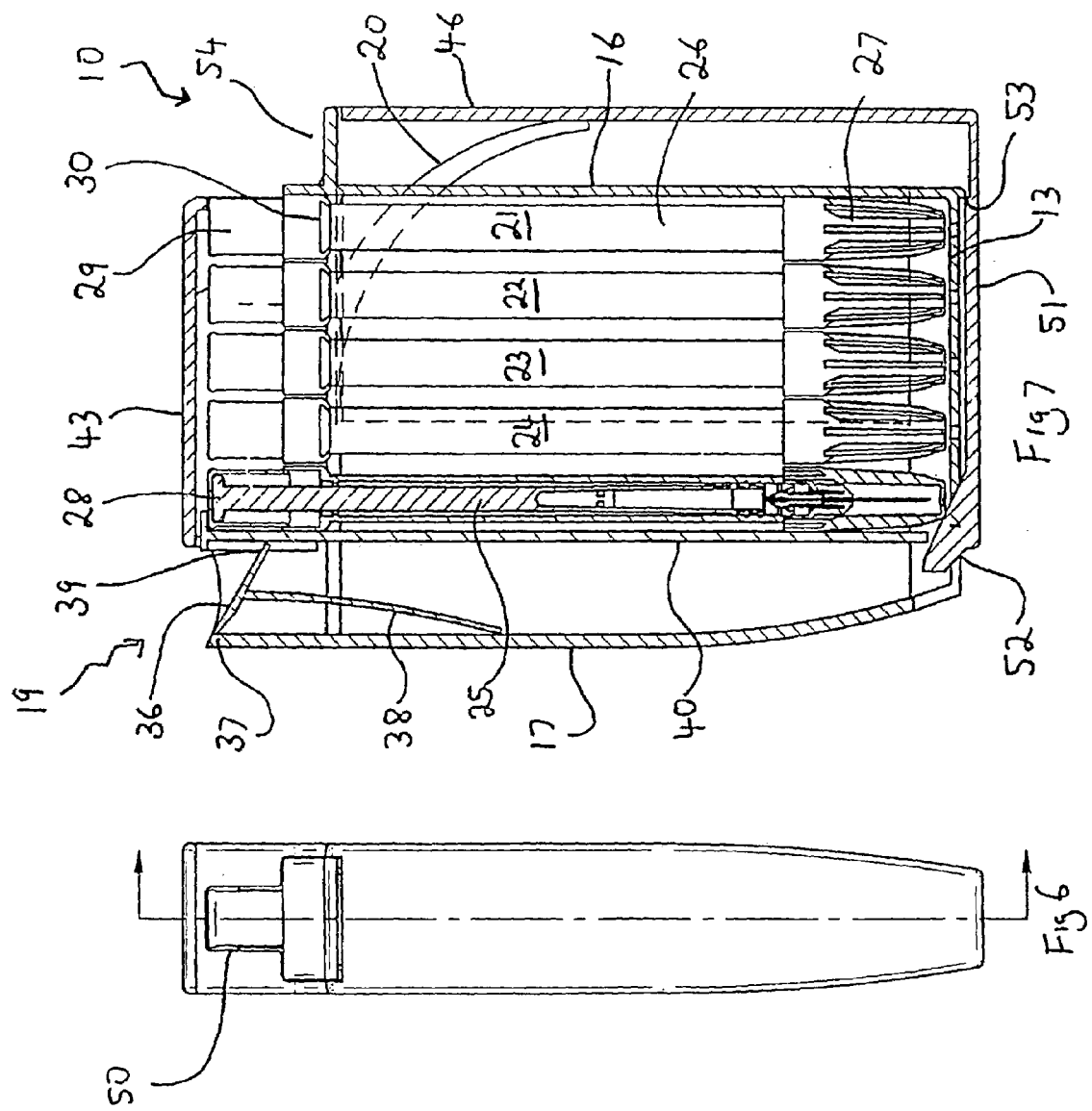

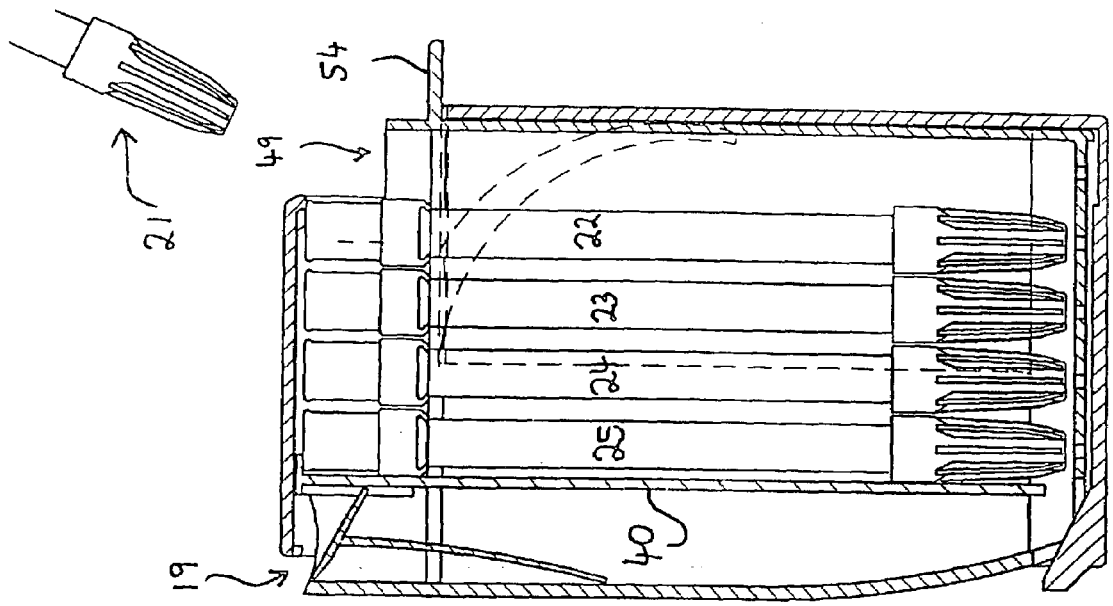
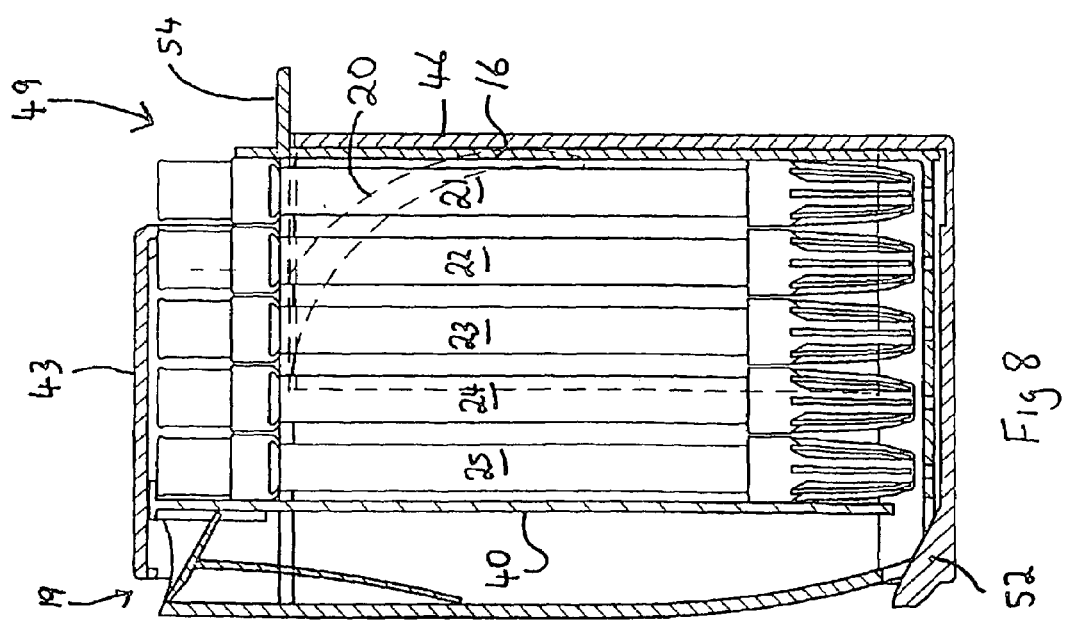

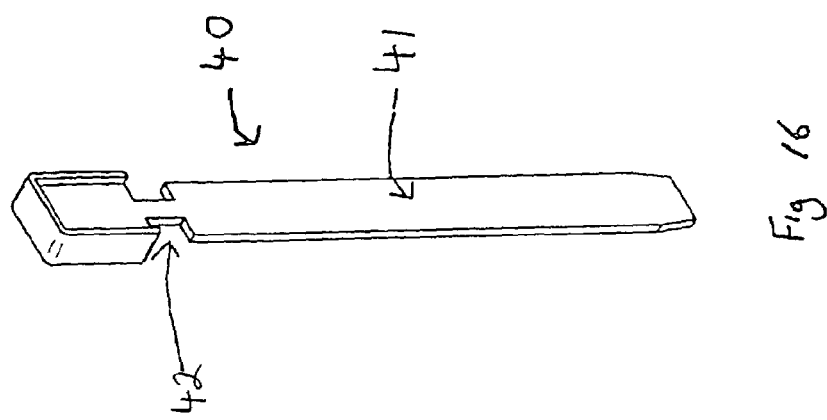
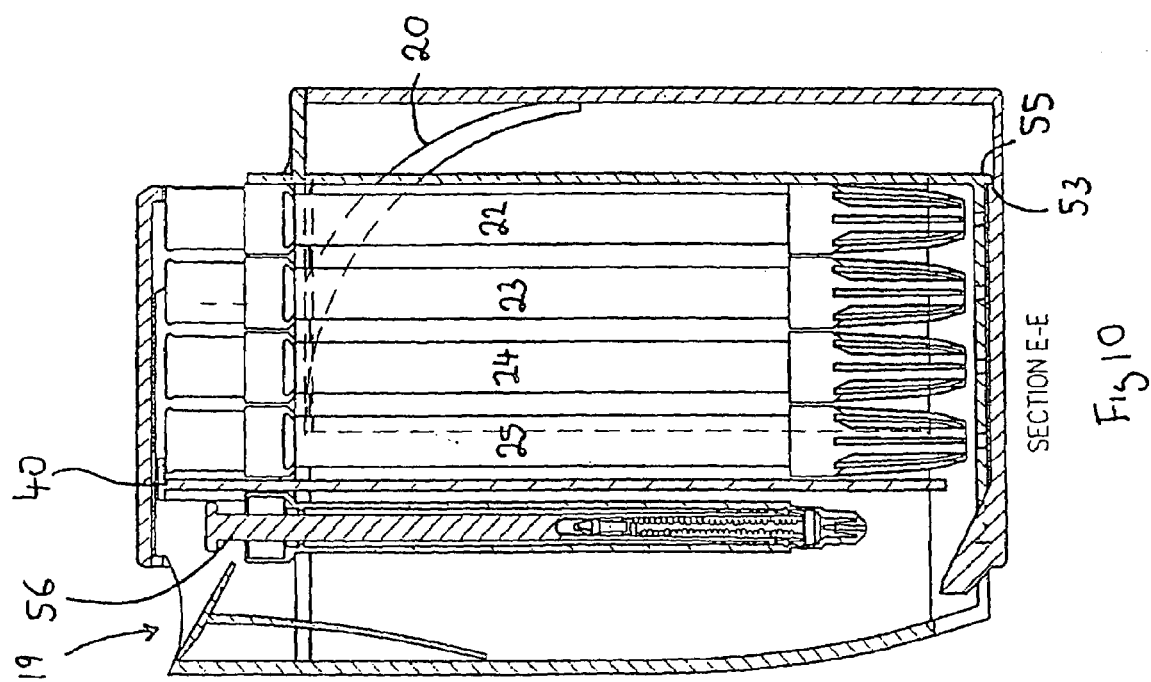

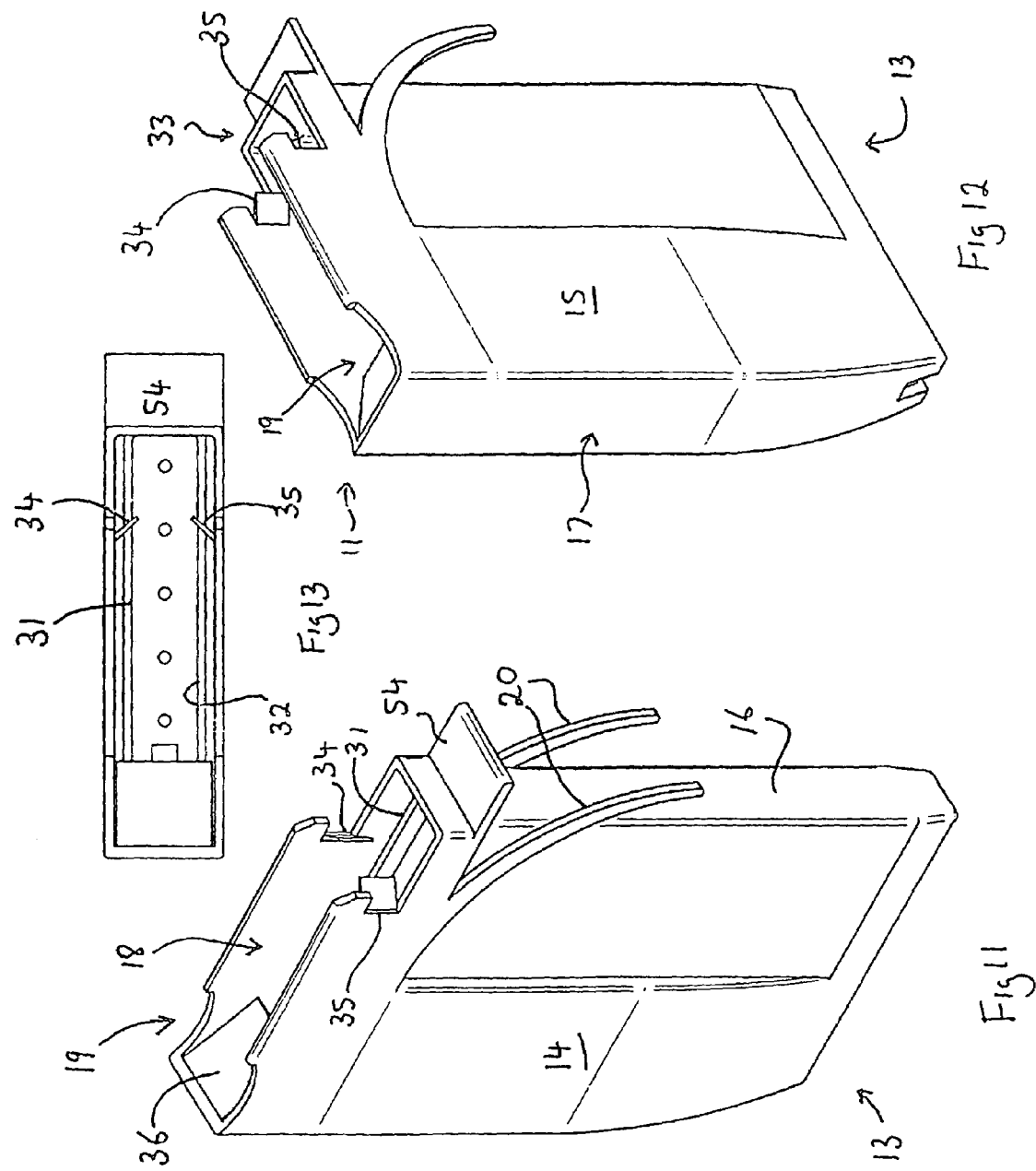

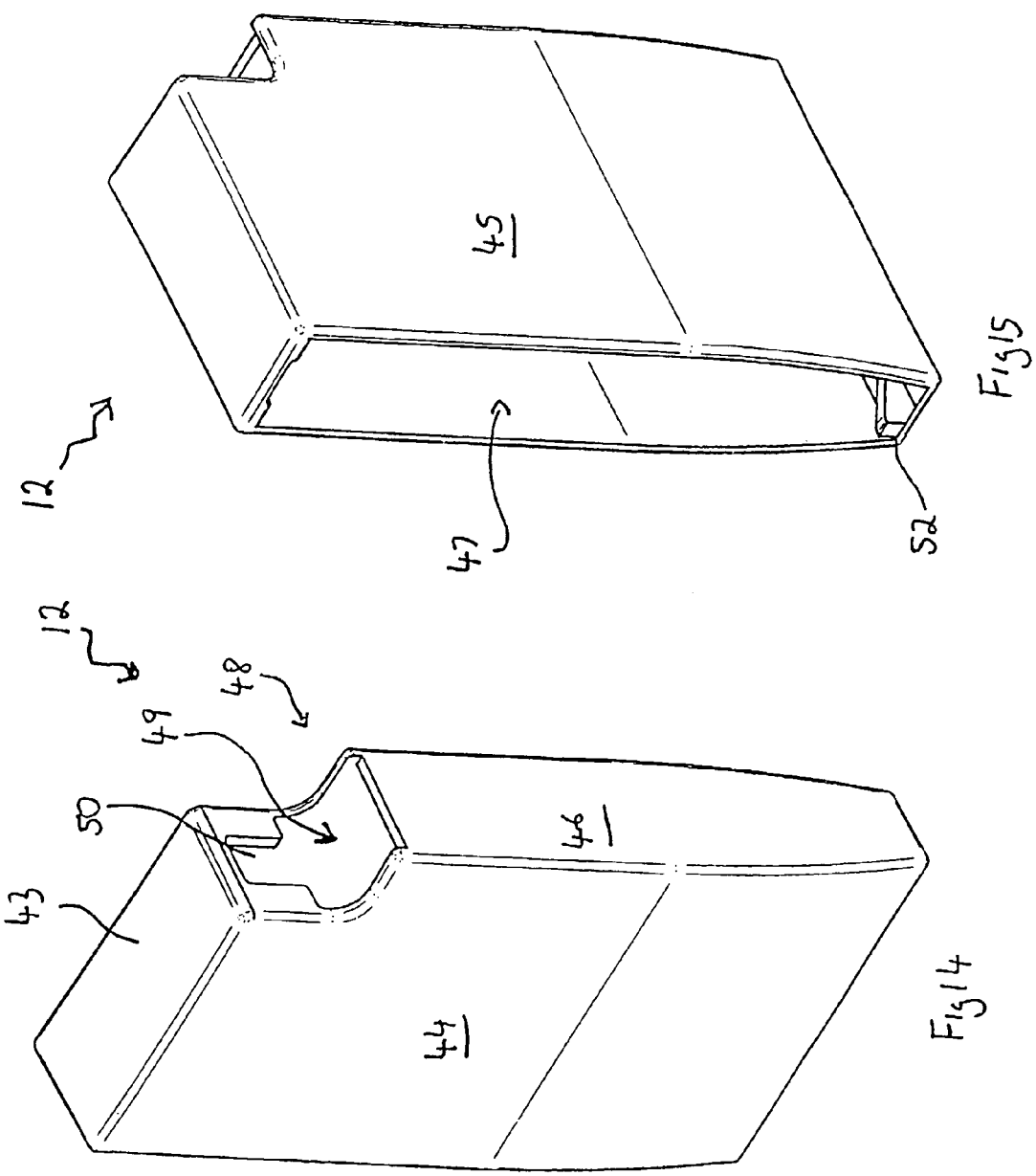

MEDICAL SYRINGE CONTAINER

FIELD OF THE INVENTION

This invention is related to a medical syringe container for holding a plurality of syringes, and which is designed to enable a new syringe to be removed from the container only when a used syringe is inserted into the container. This makes the container particularly suitable with needle exchange programs.

BACKGROUND ART

Medical syringe containers (also known as needle cases) are known in the art. The containers function to protect the syringes from damage prior to use. Typically, the container comprises a rigid housing in which a number of syringes can be held. The housing can be opened and any number of syringes can be removed. It is also possible for these containers to accommodate used syringes.

A disadvantage with these containers is that they are not particularly suitable with a needle exchange program. In a needle exchange program, a new needle (that is a syringe containing a needle) is given only when a used syringe is returned. With these known containers, there is no mechanism to ensure that a used syringe is returned prior to a new syringe being given.

There is also the temptation to try to obtain new syringes without returning used syringes. With conventional containers, there is no security against this type of abuse. Even if the container is locked it can be forced open and a new syringe can be removed.

OBJECT OF THE INVENTION

It is an object of the present invention to provide a medical syringe container which houses a number of syringes and where after the first syringe has been removed, a second syringe is not accessible until a used syringe has been returned into the container.

It is a further object of the invention to provide a medical syringe container which may overcome at least some of the above mentioned disadvantages or provide the public with a useful or commercial use.

In one form, the invention resides in a medical syringe container comprising a housing, an outlet through which a new syringe can be removed from the housing, an inlet through which a syringe can be replaced into the housing, and holding means to prevent a second syringe from being removed from the housing until a syringe has been replaced into the housing.

Thus, with this type of container, it is necessary to return a syringe (typically, a used syringe) before a new syringe can be accessed.

The container can hold a plurality of syringes and typically holds between 2 to 10 syringes. The syringes can be in a side by side relationship and are typically aligned. Thus, the syringes are typically presented in a row in the housing. It is envisaged that the housing may contain two or more rows, and it is preferred that the syringes are all in a head to head and tail to tail relationship.

The housing may comprise a top wall, a bottom wall and a pair of side walls. The syringes are typically arranged in the housing such that the top wall of the housing is above the plunger tail of the syringe and the bottom wall is adjacent the needle of the syringe.

The housing may comprise an outer housing portion and an inner housing portion. Suitably, these portions can slide relative to each other. Suitably, the inner housing portion contains the inlet and the outer housing portion contains at least part of the outlet.

In an alternative, the housing can be a one piece housing, and the top wall may be provided with the inlet. Typically, a side wall is provided with an outlet.

Guide means may be associated with the inlet to guide syringes into the housing to adopt a position which is aligned with the syringes which are in the housing. The guide means may comprise an inclined wall, face or surface associated with the inlet. Suitably, the guide means extends into the housing.

A restriction means may be associated with the inlet. The restrictions means may function to allow only syringes to be inserted through the inlet. This can reduce the likely success of a person attempting to insert an object other than a syringe to try to gain access to a new syringe. The restriction means may comprise a specially designed or "keyed" opening which can be keyed to the shape of the syringe to allow the syringe to pass through the inlet. The restriction means can also function to guide the syringe into the housing in a particular orientation, for instance, with the side tabs of the syringe extending towards each side wall when in the housing. This will be described in greater detail below.

If the housing comprises two pieces, the inner housing portion can function to hold the syringes in a side by side and aligned orientation. The inner portion may comprise a bottom wall, a pair of side walls, an inner end wall, an outer end wall, and a substantially open top. The syringes are typically supported by the inner portion in such a manner that the syringes are able to move from adjacent the outer end wall to adjacent the inner end wall. Various ways by which this can be achieved are envisaged. For instance, the inner portion may have an upper support means to support an upper part of the syringe. The upper support means may support the syringes via the tabs. The upper support means may comprise a ledge, a rail, a platform, a land portion and the like. Suitably, the support means comprises a pair of spaced apart rails, one rail being on one side wall of the inner portion and the other rail being on the other side wall of the inner portion, the rails being spaced apart such that a syringe body can slide between the rails, and the syringe is supported by the tabs which extend from each side of the syringe body.

One or both of the rails may be formed for movement relative to the other rail. Thus, in an embodiment, one or both of the rails can be slightly pushed apart to allow the forward most syringe to be removed via the outlet.

The container typically has some form of holding means. The holding means can function to prevent the syringe from moving to the outlet (and therefore being removable from the container) without a used syringe initially having been returned to the container via the inlet. The holding means can function to hold the syringes in the housing such that vigorous shaking of the housing, or hitting the housing on a hard surface does not inadvertently jolt or push a new syringe to the outlet. However, the holding means may be designed to allow a syringe to move to the outlet once a used syringe is returned into the container. Various types of holding means are envisaged. For instance, the holding means may comprise an abutment, a projection, a rib, a flap, a catch, a latch and the like which can prevent syringes from moving to the outlet. Suitably, the holding means can be moved to a free position, or deformed, bent, twisted and the like to a position where a syringe can move towards the outlet. The holding means may comprise a biased member. The biased member may be formed integrally with another part of the container, or may comprise a separate member. The separate member may compromise a small ball bearing which is biased into engagement with a syringe to prevent the syringe from moving past the ball bearing, but which can be depressed upon a force being applied to the syringe. Typically, the holding means comprises one or more deformable flaps, abutments, ridges, shoulders, ribs and the like, and these may be positioned on, above, or adjacent the support means.

The container is designed to house medical syringes of the type having a syringe body, a plunger and a needle. The container can house conventional syringes, syringes having needle stick prevention means and the like. A typical syringe having needle stick prevention means may comprise a syringe having a shoot back needle of the type which shoots back into the syringe body when the plunger is pushed into its fully forward position. One type of shoot back syringe is described in our earlier international patent application PCT/AU01/00183. However, the container need not be limited to this particular type of syringe.

In order to improve security to the container, means may be provided to render the syringes inoperative if an attempt is made to prise the container open. One suitable means comprises a syringe of special design and a container of special design. The syringe or special design typically comprises a syringe having a shoot back needle which shoots back upon forward movement of the plunger, and the container may be provided with means to trigger the shoot back mechanism should an attempt be made to force open the container. This will be described in greater detail below.

As the container can be designed to hold new needles and used needles, a partition may be provided in the container to separate the new needles from the used needles. The partition may comprise a sliding partition which is initially positioned behind the last new needle and which will progressively move along the container as used needles are placed through the inlet or partition may be brightly coloured to give a visual "empty" indication through the outlet.

BRIEF DESCRIPTION OF THE DRAWINGS

Embodiments of the invention will be described with reference to the following drawings:

FIG. 6: Illustrates an edge elevation view of the container in the position of FIG. 1a.

FIG. 7: Is a section view of the container in the position illustrated in FIG. 1a.

FIG. 8: Is a section view of the container illustrated in the position illustrated in FIG. 2a.

FIG. 9: Is a section view of the container in the position illustrated in FIG. 3a.

FIG. 10: Is a section view of the container showing a used needle inserted through the inlet and which has advanced the new syringes through the housing.

FIG. 11: Is a forward view of the inner housing portion.

FIG. 12: Is a rear view of the inner housing portion.

FIG. 13: Is a top view of the inner housing portion.

FIG. 14: Is a front view of the outer housing portion.

FIG. 15: Is a rear view of the outer housing portion.

FIG. 16: Is a view of the sliding partition.

BEST MODE

Figure 5A:
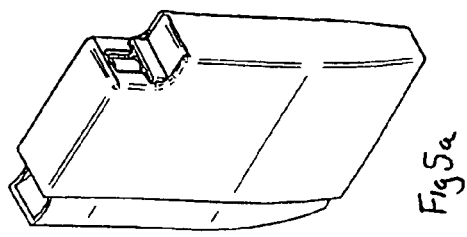
FIGS. 5a and 5b: Illustrate the container where the two parts have been moved apart to present the inlet through which a used syringe can be placed.
Figure 5B:
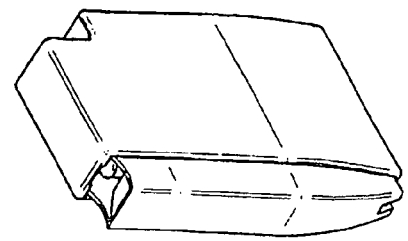

A first embodiment will be initially described with reference to figures 1–16 of the drawings. Referring initially to FIG. 7, there is illustrated a two part medical syringe container where the housing comprises an inner housing portion 11 (best illustrated in FIGS. 11 and 12), and an outer housing portion 12 (best illustrated in FIGS. 14 and 15). Inner housing portion 11 is made of rigid plastic and is substantially box like in configuration and contains a bottom wall 13, opposed side walls 14, 15, an inner end wall 16 and an outer end wall 17 and has a substantially open top 18. The inner housing portion 11 contains the inlet 19 through which a used syringe passes into the container. A biasing means in the form of a pair of spring fingers 20 extends from each side wall 14, 15 of inner housing portion 11 and extends forwardly of inner end wall 16. Fingers 20 bias against the outer housing portion 12 to allow the two portions to be squeezed together against the bias of the spring as will be described in greater detail below.

Inner housing portion 11 holds the medical syringes 21–25 and in the particular embodiment the container holds 5 syringes. Of course, it should be appreciated that the container is not to be limited to 5 syringes only.

The syringes are positioned inside the container in a side by side relationship and the syringes are all aligned which means that the needles are all together and the plunger tails are all together. In the embodiment, each syringe has a syringe body 26, a needle cap 27 (in which a needle is provided) an internal plunger having a plunger tail 28 being protected by a cap 29. Cap 29 and cap 27 ensure that the syringe remains sterile until use. Cap 29 is a deformable cap, the reason for which will be described in greater detail below.

Syringes 21–25 are supported inside inner housing portion 11 via tabs 30 which conventionally extend from each side of the syringe body and which abut against the first and second finger of the person using the syringe and depressing the plunger with the person's thumb.

The inner housing portion is provided with a support means to support the syringes in the side by side relationship illustrated in FIG. 7. The support means comprises a pair of spaced apart parallel rails 31, 32 which are best illustrated in FIG. 11 and FIG. 13. Rails 31, 32 can be formed integrally with the inner housing portion and are spaced part sufficiently to allow the syringe body 26 to slide between rails 31 and 32. Rails 31, 32 support the tabs 30 on each syringe which means that the syringe can slide along the inner housing portion from adjacent outer end wall 17 towards inner wall 16.

The open top 18 forms part of the outlet portion 33 (see FIG. 12) of the container. Rails 31, 32 extend along the outlet portion 33 which means that a syringe is able to slide along the rails to outlet portion 33 and therefore able to be removed from the container. A holding means is and provided to prevent the second syringe 22 from being removed from the housing until a used syringe has been replaced into the housing. In the embodiment, the holding means comprises a pair of inwardly inclined resilient hold back tabs 34, 35 (FIGS. 11–12) which are positioned above rails 31, 32 and which are attached to side walls 14, 15. Tabs 34, 35 will hold back the syringes in inner housing portion 11 from sliding towards outlet portion 33. However, tabs 34, 35 can be deformed outwardly if the syringes behind the tabs are pushed hard enough by the action of a used syringe being inserted through inlet 19. Thus, the function of tabs 34, 35 is to hold back new syringes until a used syringe is pushed through inlet 19. This will be described in greater detail below.

Inlet 19 is provided with a guide means which is in the form of an angled flap 36. Flap 36 is also illustrated in FIG. 7 and is hinged to the top of outer end wall 17 at hinge point 37. Flap 36 is biased to a partially depending (open) position illustrated in FIG. 7 by a biasing finger 38. The function of flap 36 is to guide a used syringe into and towards the new syringes in the inner housing portion 11 and also to provide a biasing action or pushing action against the used syringe as it is inserted through inlet 19. Once the used syringe has been fully inserted into inner housing portion 11, flap 36 moves to the position illustrated in FIG. 10 and the lower most free edge 39 of flap 36 is above the tabs 30 of the syringe and therefore the syringe cannot be pulled back out of inlet 19.

Flap 36 provides a resistance to the insertion of the needle.

This requires the needle to be forced in by pushing on the plunger. This action can "trigger" the shoot back mechanism of a syringe. Thus if a syringe is used but the shoot back mechanism has not operated, or if an unused syringe is inserted through the inlet, it will be rendered inoperative by "triggering" the shoot back mechanism.

Inlet 19 can also be provided with a restriction means to prevent or reduce insertion of an object other than a used syringe through inlet 19. Typically, the restriction means comprises an opening configured or "keyed" such that only the particular shape of a syringe can pass through inlet 19.

A partition wall 40 is provided in portion 11, and partition wall 40 is best illustrated in FIG. 16. Partition wall 40 has a main body portion 41 which separates a new syringe from a used syringe, and a necked portion 42 which allows the partition to ride along rails 31, 32.

The container includes an outer housing portion 12 best illustrated in FIGS. 14 and 15. Outer housing portion 12 has a substantially box like configuration and includes a top closed wall 43, a pair of opposed side walls 44, 45, a substantially closed front wall 46 and a substantially open rear end 47. The forward end of top wall 43 and an upper portion of front wall 46 define a step which defines part of outlet 49. Outlet 49 has a restricted top portion 50. The outer housing portion has a substantially closed bottom wall 51. Bottom wall 51 (best illustrated in FIG. 7) has a rear ramped portion 52 which forms part of the means to render a syringe inoperative should an attempt be made to force open the container and which will be described in greater detail below.

Bottom wall 51 has a forward stop or shoulder 53 which defines the distance by which the inner housing portion and the outer housing portion can be squeezed together.

Figure 1A:
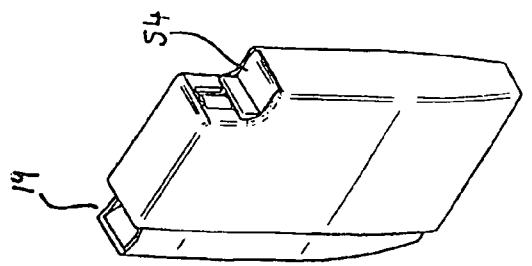
FIGS. 1a and 1b: Illustrate a forward view and a rear view of a two part container filled with syringes (not illustrated) and in the initial position.
Figure 1B:
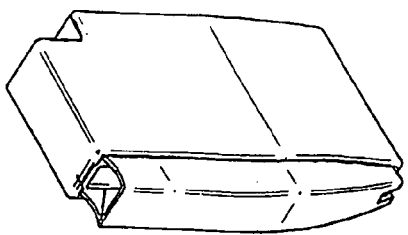

Initially, the container is as illustrated in FIG. 7 and FIG. 1a and contains 5 new sterile syringes. Outlet 49 is substantially covered by tab 54 which extends forwardly of inner end wall 16 of the inner housing portion 11 and best illustrated in FIGS. 11 and 12.

Figure 4A:
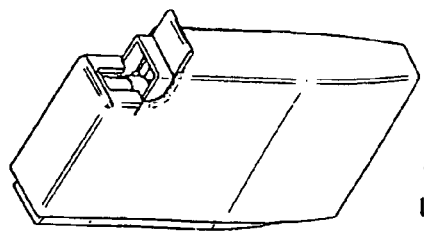
FIGS. 4a and 4b: Illustrate how further squeezing of the container will not present a second needle as a used needle has not yet been inserted into the container.
Figure 4B:
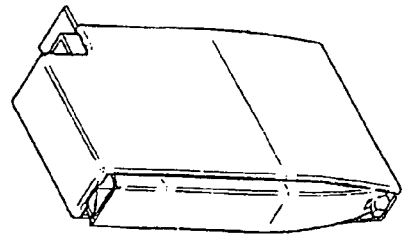
Figure 3A:
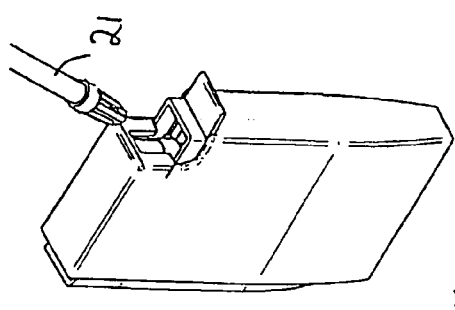
FIGS. 3a and 3b: Illustrate the container with the first syringe having been removed from the outlet.
Figure 3B:
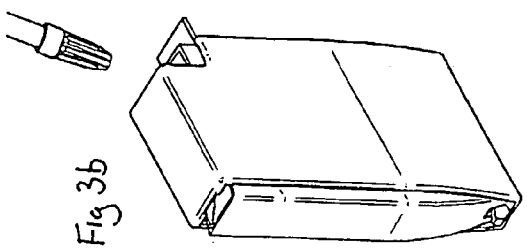
Figure 2A:
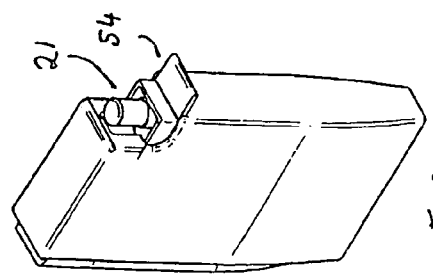
FIGS. 2a and 2b: Illustrate the two part container where the two parts have been squeezed together to present the first new syringe at the outlet.
Figure 2B:
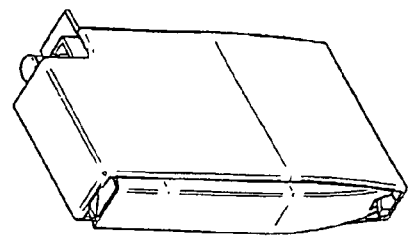

The sequential operation to remove a new syringe is illustrated in FIGS. 1–5 and will be described as follows:

To remove the first new syringe, the outer housing portion 12 and the inner housing portion 11 are squeezed together and this can be done in a one handed operation. The two portions are biased away from each other by fingers 20 as fingers 20 bias against front wall 46 of outer housing portion 12. When the two portions are squeezed together the container adopts the position illustrated in FIGS. 2a and 2b and also FIG. 8. In this position the first syringe 21 has been pushed forwardly and now extends into outlet 49. Tab 54 has been pushed forwardly as it is attached to the front of inner housing portion 11. Syringe 21 can now be pulled out of outlet 49 by a person's fingers. Importantly, the first syringe 21 sits forwardly of the hold back tabs 34, 35 and therefore can be removed. The remaining syringes 22–25 sit behind the hold back tabs 34, 35 and are therefore unable to advance forwardly over rails 31, 32 to the outlet. Thus, and as illustrated in FIG. 4a and FIG. 9, once the first syringe has been removed, the remaining syringes 22–25 stay in position.

The grip on the container can then be relaxed which will cause the inner housing portion 11 to now be pushed back to its initial position (by the action of spring fingers 20), and this will also result in tab 54 being returned to lie substantially over outlet 49. This is the position illustrated in FIG. 5a which is identical to the position illustrated in FIG. 1a except that the container now contains 4 syringes as 1 syringe has been removed.

Importantly, if the container is again squeezed such that the inner housing portion and the outer housing portion are squeezed together, syringe 22 does not present itself to outlet 49 as it is held back by tabs 34, 35. Therefore, once the first syringe has been removed subsequent syringes are not available for removable.

The inner housing portion is prevented from moving entirely out of outer housing portion by a bottom lip 55 which abuts against the step 53 on the bottom wall of outer housing portion.

To advance new syringe 22, past the hold back tabs 34, 35 and therefore towards outlet 49 it is necessary to return a syringe (typically a used syringe) through inlet 19. This is best illustrated in FIG. 10. Used syringe 56, best illustrated in FIG. 10, has been pushed through inlet 19 and has been guided into the position where it is in a parallel orientation relative to new syringes 22–25 by virtue of flap 36. As the used syringe 56 is pushed through inlet 19, it abuts against internal partition wall 40 and forces wall 40 to move forwardly. This action causes each new syringe 22–25 to move forwardly by a distance equivalent to the width of the used syringe 56. This forward force causes the second new syringe 22 to be pushed past hold back flaps 34, 35 and thus makes the second new syringe available for removal when the outer housing portion and the inner housing portion are again 30 squeezed together.

Once the second new syringe 22 has been removed, the hold back flaps 34, 35 will prevent the remaining new syringes from being removed until a second used syringe has been inserted through inlet 19.

The sequence can be repeated until all the new syringes have been removed and the container now contains the used syringes.

The container of the particular embodiment also has a means to render the new syringes inoperative should an attempt be made to pull inner housing portion 11 out of outer housing portion 12. This means requires the syringes to be of the type having a shoot back needle and this type of syringe is described in our earlier international patent application PCT/AU01/00183, but other shoot back syringes can also be used. These syringes operate by biasing the needle into the shoot back position and having some form of needle retaining means which prevents the needle from shooting back until the plunger has been fully advanced. Once the plunger has been fully advanced, the retaining means is removed and the needle shoots back. In the embodiment, bottom wall 51 of outer housing portion 12 is provided with an upwardly inclined ramped portion 52 this being illustrated in FIGS. 7, 15 and 10. Each new syringe is provided with a cap 29 to render the syringes sterile, but importantly, cap 29 can be deformed under pressure to force the plunger fully forward which will cause the needle to shoot back therefore rendering the syringe inoperative. Thus, should an attempt be made to pull inner housing portion 11 out of housing portion 12, the new syringes will ride over ramped portion 52 causing the syringes to move upwardly which in turn causes the cap 29 of the plunger to deform which causes the plunger to move fully into the syringe body which triggers the shoot back needle thereby rendering the needles inoperative.

FIGS. 17–23 illustrate a second embodiment of the invention. In this embodiment, the medical syringe container comprises a single housing 60 which has a closed bottom wall 61, a closed end wall (called the inner end wall for the sake of convenience) 62, a pair of closed opposed side walls 63, 64 (in the embodiment illustrated, one of the side walls has been removed to allow the internal components of the container to be viewed), a substantially closed top wall 65, and an open end wall 66 (called the outer end wall for the sake of convenience).

Top wall 65 contains an inlet 67, and the open outer end wall 66 comprises the outlet (which shall be given reference numeral 68 for the sake of convenience). Container 60 is provided with a support means to support a plurality of syringes in the container. In the particular embodiment, 5 syringes 69–73 are illustrated although it should be appreciated that no limitation is meant thereby.

Figure 18:
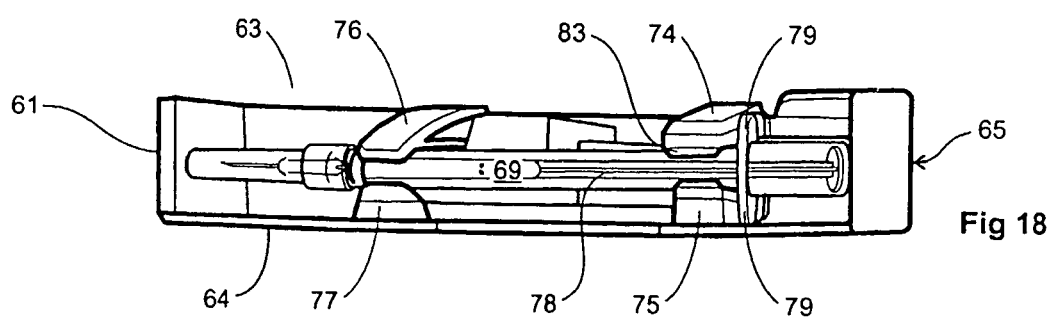
FIG. 18: Is an edge elevation view of the container of FIG. 17.
Figure 19:
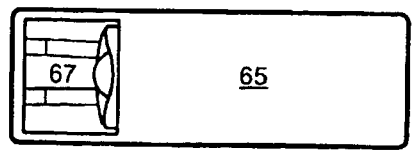
FIG. 19: Is a plan view of the container of FIG. 17.

The support means comprises a pair of spaced apart rails 74, 75 (best illustrated in FIG. 18). In this particular embodiment, the syringes are supported by an upper support means comprising a pair of rails 74, 75 and a lower support means comprising a pair of rails 76, 77. One of the rails 75, 77 is formed integrally or is rigidly fixed to a respective side wall, or the other of the rails 74, 76 is cantilevered and can move towards and away from the other rail member 75, 77. Rails 74, 75 are spaced apart by a distance sufficient to allow the syringe body 78 to slide between the rails. The tabs 79 on the syringes extend above rails 74, 75 and support the syringes in the container.

Figure 17:
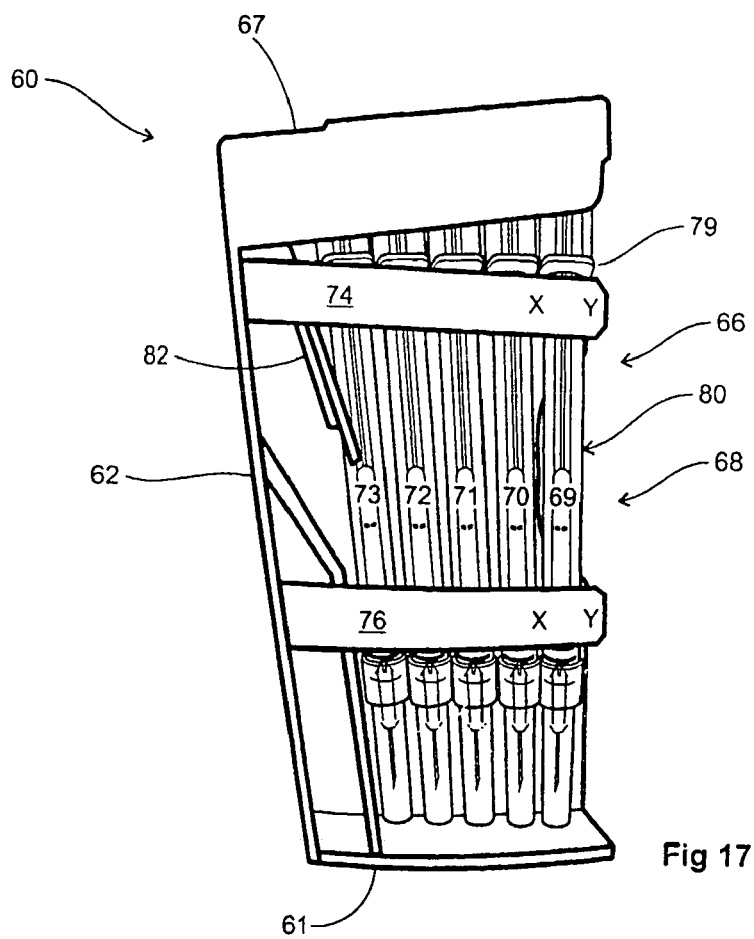
FIG. 17: Illustrates a medical syringe container according to a second embodiment of the invention and which contains a one piece housing and which is illustrated in cutaway view.

Rails 74, 75 are provided with holding means which comprise small projections or tabs which prevent the syringes from sliding from the position illustrated as x in FIG. 17 to the position illustrated as y in FIG. 17.

Figure 20:
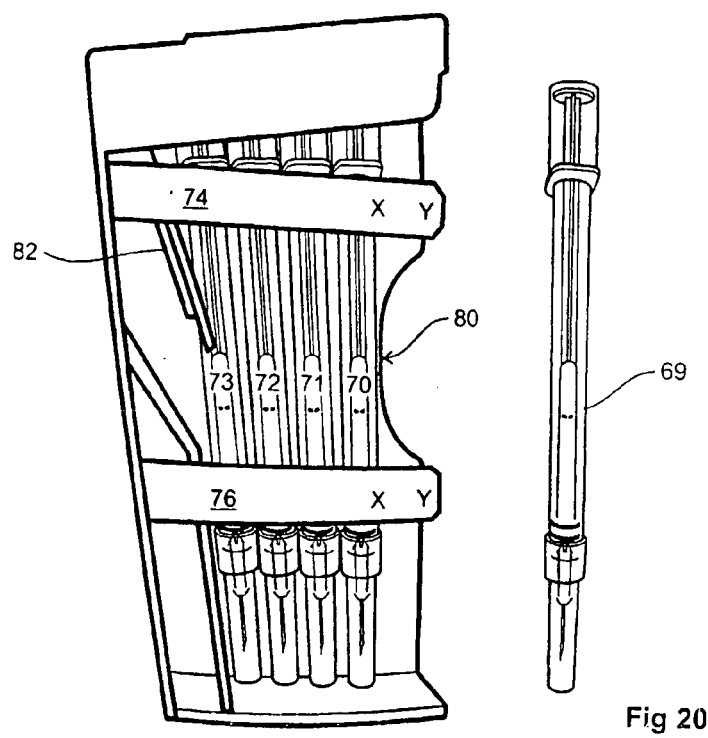
FIG. 20: Illustrates the container of FIG. 17 with the first new syringe removed from the container and illustrating that the second syringe does not move forwardly.
Figure 21:
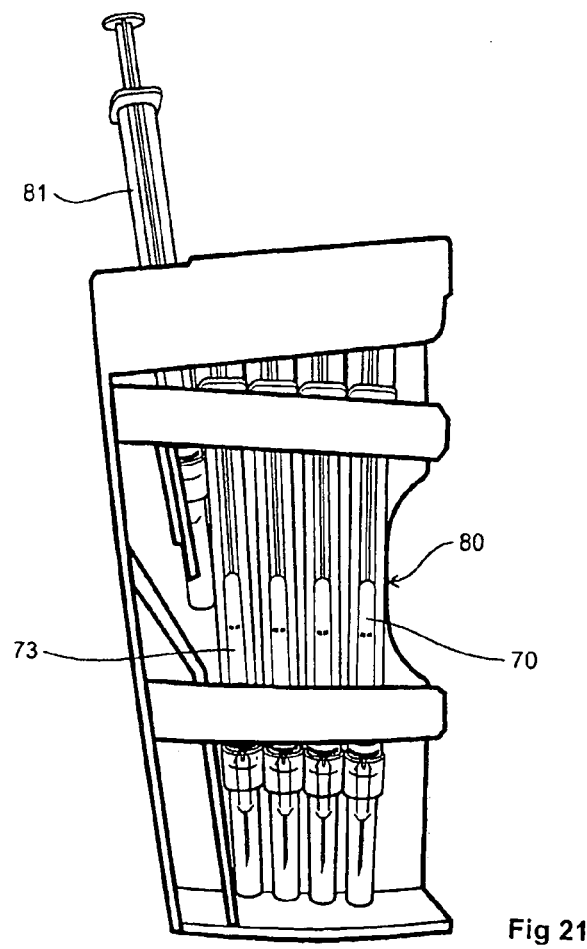
FIG. 21: Illustrates the container of FIG. 20 with a used syringe being inserted through the inlet.
Figure 22:
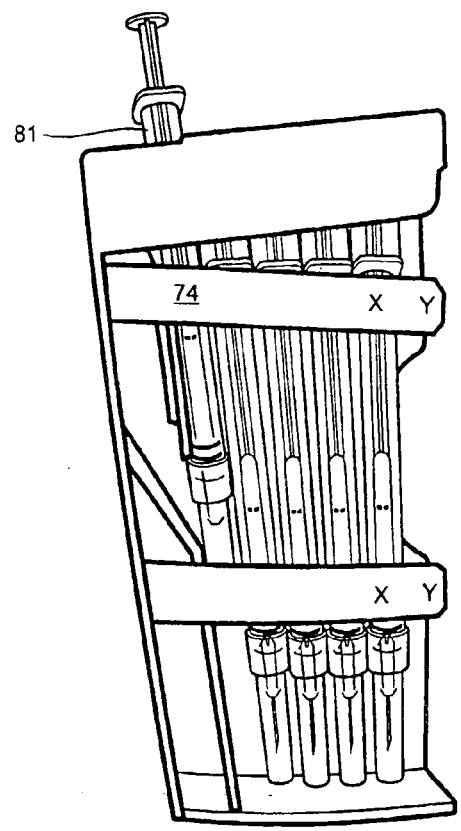
FIG. 22: Illustrates the container of FIG. 21 with a used syringe moved further into the inlet and beginning to push forwardly the new syringes in the container.
Figure 23:
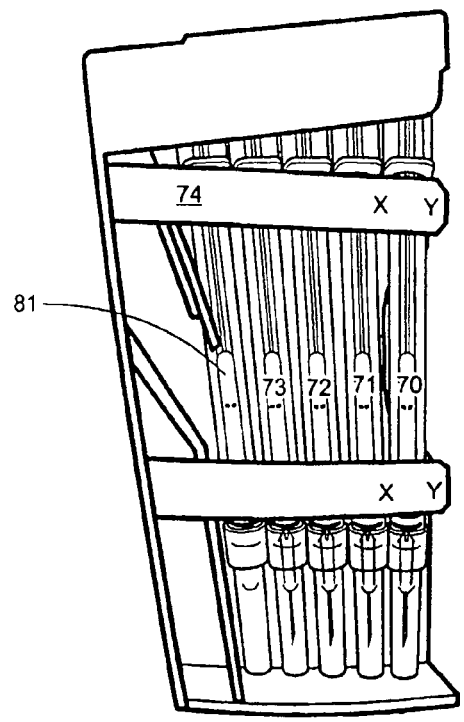
FIG. 23: Illustrates the container of FIG. 22 with a used syringe fully inserted into the container and the next new syringe now been available for removable.

In use, the first new syringe 69 can be simply pulled out of outlet 68 as the side walls are provided with a recessed portion 80 which is illustrated in FIG. 17 and FIG. 20. Recessed portion 80 allows the first syringe 69 to be gripped around the syringe body by a person's fingers and removed from the container. Importantly, the second syringe 70 does not advance forward from position x to position y as it is held at position x by the holding means. A used syringe 81 (see FIGS. 21–23) needs to be pushed through inlet 67 before the second new syringe 70 can be advanced to the position y thereby allowing the second new syringe 70 to be removed. Sequentially, the new syringe 81 is pushed through inlet 69 and is guided into engagement with the syringes in the housing by a guide means 82 which comprises a biased flap. As the syringe 81 is pushed further through inlet 67 it places a pushing force against the back of syringe 73 and therefore against each of the other syringes in the container. Once the new syringe 81 has been pushed fully into the container, the pressing action against the other syringes is sufficient to force the second new syringe 70 past the hold back means at position x and into position y where it can now be removed from outlet 68. The forward most edge in position y is also provided with a small inwardly turn tab or lift 83 (see FIG. 18) to prevent the new syringe from simply falling out of the container on a slight shake. Instead, the syringe needs to be grasped by a person's finger and pulled out of the container against the action of the small lip 83.

It should be appreciated that various changes and modifications can be made to the embodiment described without departing from the spirit and scope of the invention. For instance, the container may contain a visual means such as a window to visually identify the number of new syringes in the container.

The invention claimed is:

1. A medical syringe container comprising a housing, at least one medical syringe in the housing, an outlet through which an unused syringe can be removed from the housing, an inlet through which a syringe can be replaced into the housing, said housing comprising two parts including an inner housing portion and an outer housing portion which are adapted to be squeezed together, biasing means to bias the housing portions away from each other, said inner housing portion including a syringe support, said syringe support retaining the syringes in a side by side relationship that allows the syringes to move from the inlet to the outlet, said syringe support comprising a pair of spaced apart rails adapted to support a syringe by laterally extending tabs which extend from the syringe, said rails being spaced apart by a distance sufficient to allow a syringe body to slide along the rails, and holding means to prevent a second unused syringe from being removed from said housing until a syringe has been replaced into the housing, wherein replacement of the syringe into the housing causes the second unused syringe to move past said holding means and to the outlet to enable removal of the second unused syringe through the outlet.

2. The container of claim 1, wherein the holding means is a resilient tab which prevents a syringe from passing to the outlet, the tab allowing a syringe to move past the tab when a syringe has been replaced into the housing.

3. The container of claim 1, wherein the inlet contains guide means to guide a returned syringe into the housing.

4. The container of claim 3, wherein the guide means is an incline extending and depending from one edge of the inlet.

5. The container of claim 1, comprising a restriction means adjacent the inlet to allow only a syringe to pass through the inlet.

6. The container of claim 1 which is adapted to hold between 2–10 syringes in a side by side relationship.

7. The container of claim 1, including a partition in the housing, the partition functioning to separate the used syringe being returned into the container from the new syringes in the container.

8. The container of claim 1, wherein the syringes are single use syringes of the type having a shoot back needle which is activated to shoot back upon pressing of the syringe plunger, the inlet of the container being provided with activation means to activate the shoot back mechanism of the syringe upon insertion of a returned syringe into the container, to ensure that all returned syringes are rendered inoperative.

9. The container of claim 8, wherein the activation means is a flap adjacent the inlet which provides a resistance to insertion of the syringe, thereby requiring the syringe to be forced in by pushing on the plunger which will activate the shoot back mechanism of a returned syringe which has not yet been rendered inoperative.

* * * * *